United States Patent
Park et al.

(10) Patent No.: US 7,451,058 B2
(45) Date of Patent: Nov. 11, 2008

(54) ADAPTIVE PACE ESTIMATION DEVICE AND METHOD

(75) Inventors: Kyong-Ha Park, Suwon-si (KR); Hyun-Su Hong, Seongnam-si (KR); Jae-Myeon Lee, Suwon-si (KR); Hee Jung, Ansan-si (KR); Chan-Gook Park, Seoul (KR)

(73) Assignees: Samsung Electronics Co., Ltd (KR); Seoul National University Industry Foundation (KR)

( * ) Notice: Subject to any disclaimer, the term of this patent is extended or adjusted under 35 U.S.C. 154(b) by 0 days.

(21) Appl. No.: 11/706,856

(22) Filed: Feb. 15, 2007

(65) Prior Publication Data
US 2007/0208532 A1     Sep. 6, 2007

(30) Foreign Application Priority Data
Feb. 15, 2006    (KR)  ............... 10-2006-0014863

(51) Int. Cl.
*G01P 7/00*        (2006.01)
(52) U.S. Cl. .................................... 702/142; 702/141
(58) Field of Classification Search .......... 702/414–142
See application file for complete search history.

(56) References Cited

U.S. PATENT DOCUMENTS

| | | | |
|---|---|---|---|
| 6,522,266 B1 * | 2/2003 | Soehren et al. | 340/988 |
| 2003/0018430 A1 * | 1/2003 | Ladetto et al. | 701/217 |
| 2003/0236614 A1 * | 12/2003 | Yamakita et al. | 701/207 |

* cited by examiner

*Primary Examiner*—Bryan Bui
*Assistant Examiner*—Jonathan Moffat
(74) *Attorney, Agent, or Firm*—The Farrell Law Firm, PC

(57) ABSTRACT

A device and method for estimating an adaptive pace depending on a user with a different pace. An adaptive pace estimation device includes a GPS receiver for receiving position information from a GPS satellite; an acceleration sensor for measuring vibrations due to walking to output an acceleration value; a memory for storing an instruction data set with a walking pattern representative value updated in accordance with an instruction corresponding to at least one walking pattern group; and an instruction data generator for calculating a mean value of input walking pattern data and updating a value approximate to the mean value of the input walking pattern data and the walking pattern representative value as a walking pattern representative value.

13 Claims, 9 Drawing Sheets

025 # ADAPTIVE PACE ESTIMATION DEVICE AND METHOD

PRIORITY

This application claims priority to an application filed with the Korean Intellectual Property Office on Feb. 15, 2006 and assigned Serial No. 2006-14863, the contents of which are incorporated herein by reference.

BACKGROUND OF THE INVENTION

1. Field of the Invention

The present invention relates to a walking pace estimation device and method, and more particularly to a device and method for estimating an adaptive pace depending on users with different paces.

2. Description of the Related Art

In general, walking pace estimation can be detected through an accelerometer that shows a change in acceleration for an impact transmitted whenever a person with a terminal having an attached sensor capable of measuring acceleration takes a step. In order to detect a precise step, the change in acceleration should be precisely measured. A process for linearly combining output values of an acceleration sensor to detect acceleration changes is generally used to estimate a pace.

A process currently used for pace estimation uses a neural network instructed in a pace with a specific velocity. A substantial error rate for a pace with a specific velocity does not occur when the neural network has been instructed. However, a large error rate for a pace with a specific velocity can occur when the neural network has not been instructed. Since the pace of a person varies, it is likely that an error will occur when the process has been instructed in one pace and is applied as described above.

In order to examine whether a neural network can adapt to a user's walking pattern when it has not been instructed, an experimental value for a specified pace will be discussed through a second experimenter different from a first experimenter having instructed the neural network off line. It is assumed that the second experimenter has physical characteristics and a walking behavior different from the first experimenter. The second experimenter produces two sets for each group, the sets being classified into fast, normal and slow paces, i.e., for a total of six data sets. Such a data set is composed of an acceleration dispersion and a walking frequency for each step. When errors generated in a case where data of the second experimenter is applied to the neural network having been instructed in the pace of the first experimenter are applied to the six data sets, errors can be represented as shown in Table 1.

TABLE 1

|  | Fast Pace 1 | Normal Pace 1 | Slow Pace 1 | Fast Pace 2 | Normal Pace 2 | Slow Pace 2 |
| --- | --- | --- | --- | --- | --- | --- |
| Error Percentage (%) | 7.48 | 6.06 | 0.12 | 7.12 | 8.60 | 4.43 |

Since there occurs an error of about 10% when estimating a user's pace when the neural network has not been instructed, it can be seen that an instruction is required for the purpose of estimating a precise pace. If the neural network is renewed whenever a Global Positioning System (GPS) signal is received due to the amplitude of a walking frequency of about 3 Hz when GPS information is calculated from a GPS signal received at 1 Hz, data for instructing can be obtained. A condition is set so this data is immediately used in the instruction of the neural network. One set of fast, normal and slow paces in the six data sets produced by the second experimenter are used in an online instruction, and errors are obtained with the rest of the sets whenever transmission intensity is renewed each time. If the number of updated data is changed, changes in error can appear as shown in FIGS. 1 to 3. Here, the x-axis denotes the sequential number of updates and the y-axis denotes the size of an error. The graphs of FIGS. 1 to 3 show changes in error for the respective data sets of fast, normal and slow paces, which are used in verification. As can be seen through the graphs of FIGS. 1 to 3, in a case where the respective data sets are sequentially used in instruction, they are renewed with transmission intensity suitable for data only in their own instruction areas.

That is, when the neural network has been instructed in the fast pace, it outputs a precise pace only for the acceleration dispersion and walking frequency of the fast pace data set. Similarly, when the neural network has been instructed in the normal or slow pace, it outputs a precise pace only for the acceleration dispersion and walking frequency of the normal or slow pace data set.

As described above, individuals normally walk with paces falling within a narrow pace area. They continue to step fast in a condition of stepping fast, and continue to step slow in a condition of stepping slow. Thus, in a case where a neural network having been instructed in a pace with a specific velocity is used, there is a problem in that substantial pace errors can occur in an applied condition where instructions regarding the pace with an instructed velocity are not performed. Further, a pace estimation using a GPS receiver is possible in a position where a GPS signal can be received, while it is impossible in a position where a GPS signal cannot be received.

SUMMARY OF THE INVENTION

Accordingly, the present invention has been made to solve the above-mentioned problems occurring in the prior art, and it is an object of the present invention to provide a pace estimation device and method for detecting an adaptive pace depending on a user with a different pace.

It is another object of the present invention to provide a pace estimation device and method, wherein a user's walking pattern is instructed at a position where a GPS signal can be received so that a user's optimized walking pattern is obtained, and a user's pace is estimated using the user's optimized walking pattern to yield a moving distance at a position where a GPS signal cannot be received.

In order to accomplish these objects of the present invention, according to an aspect of the present invention, there is provided an adaptive pace estimation device, which includes a GPS receiver for receiving a position information from a GPS satellite; an acceleration sensor for measuring vibrations due to walking to output an acceleration value; a memory for storing an instruction data set with a walking pattern representative value updated in accordance with an instruction corresponding to at least one walking pattern group; and an instruction data generator for calculating a mean value of input walking pattern data and selecting an approximate value to the mean value from the input walking pattern data and the walking pattern representative value to update the value as a walking pattern representative value.

In order to accomplish these objects of the present invention, according to another aspect of the present invention, there is provided a method for estimating a pace in a communication terminal provided with a GPS receiver for receiving position information from a GPS satellite and an acceleration sensor for measuring a vibration due to walking so as to output an acceleration value, the method including storing an instruction data set with a walking pattern representative value updated in accordance an with instruction corresponding to at least one walking pattern group; calculating a mean value of input walking pattern data; and selecting an approximate value to the mean value of the input walking pattern data and the walking pattern representative value to update the approximate value as a new walking pattern representative value.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
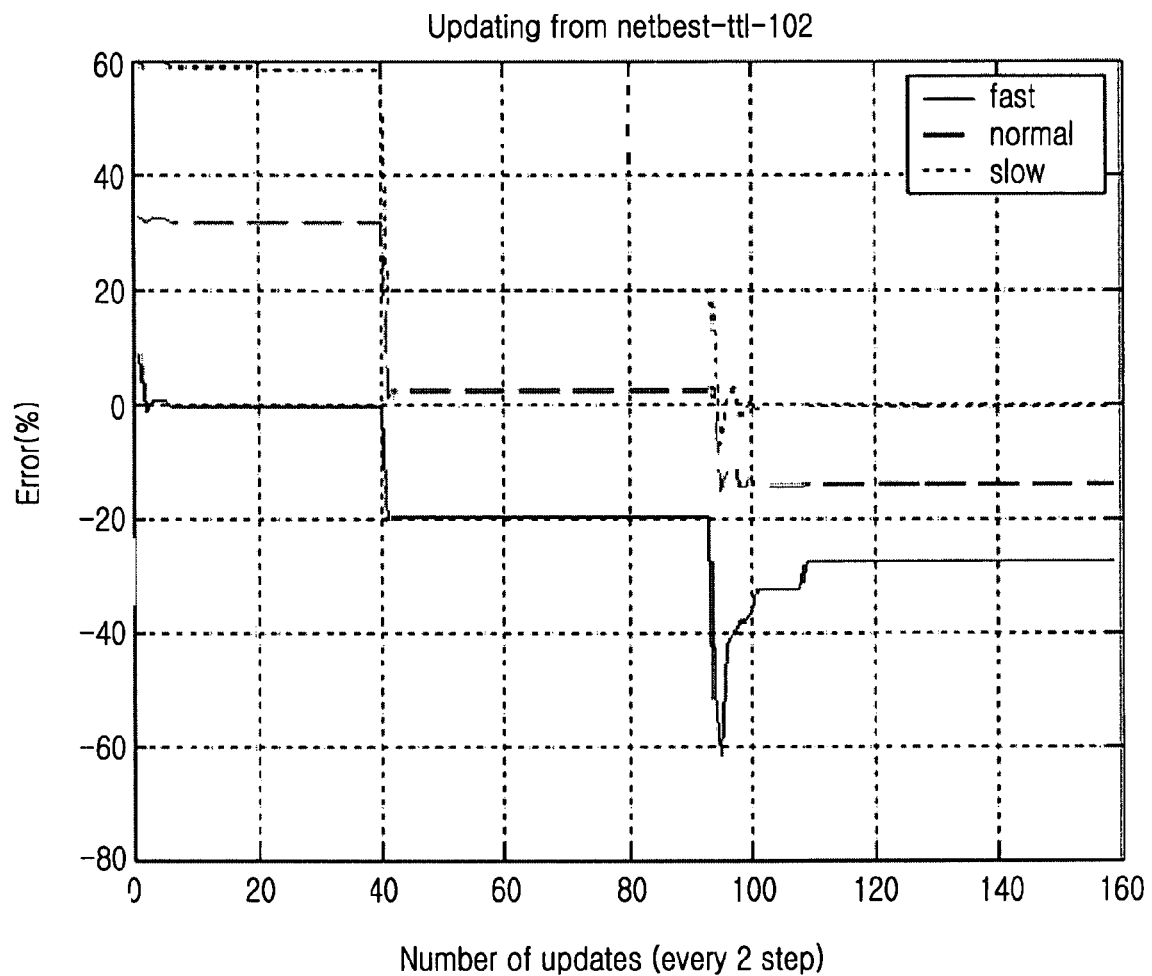
FIGS. 1 to 3 are views illustrating a change in error generated when estimating a pace with a walking pattern of a general walker as an input using instructed data for a pace with a specific velocity.
Figure 2:
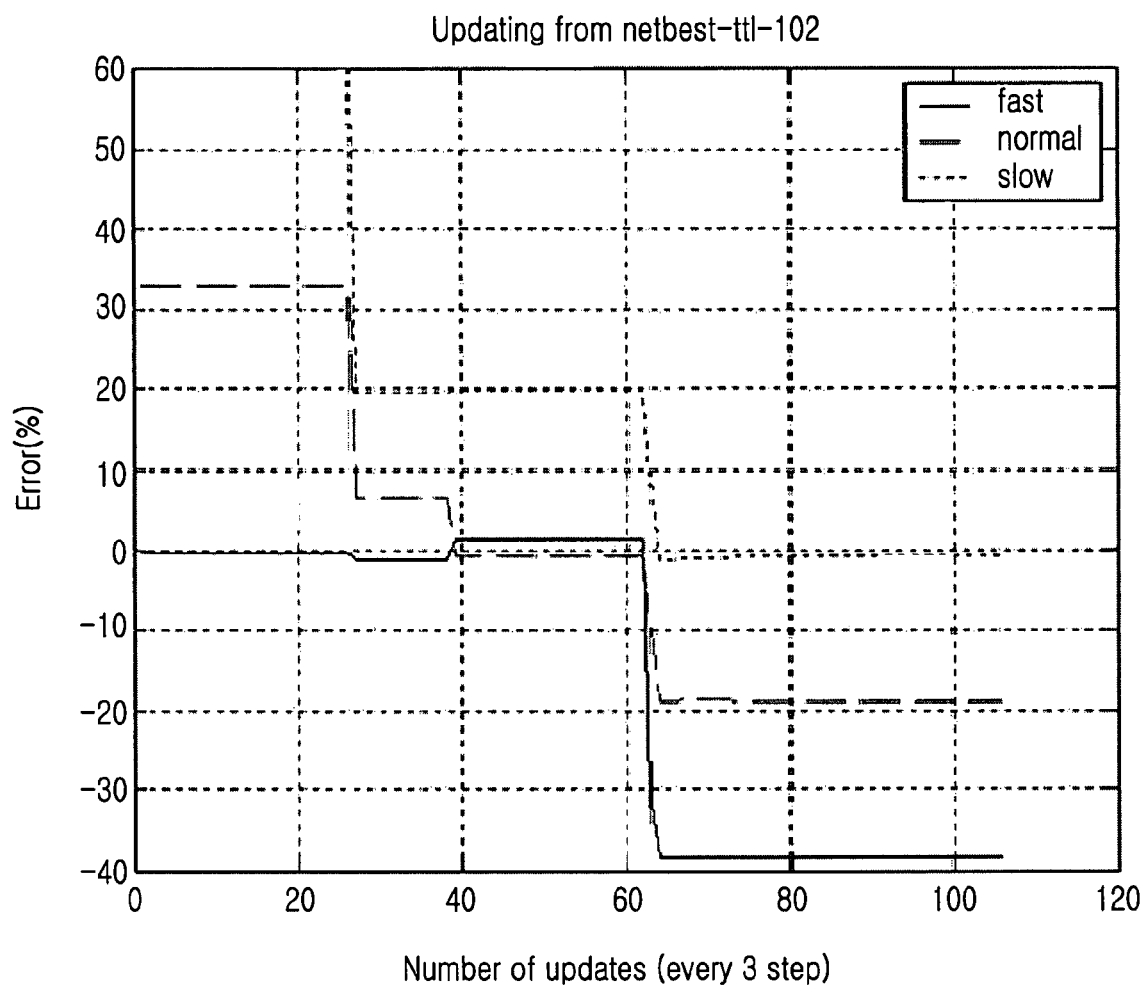
Figure 3:
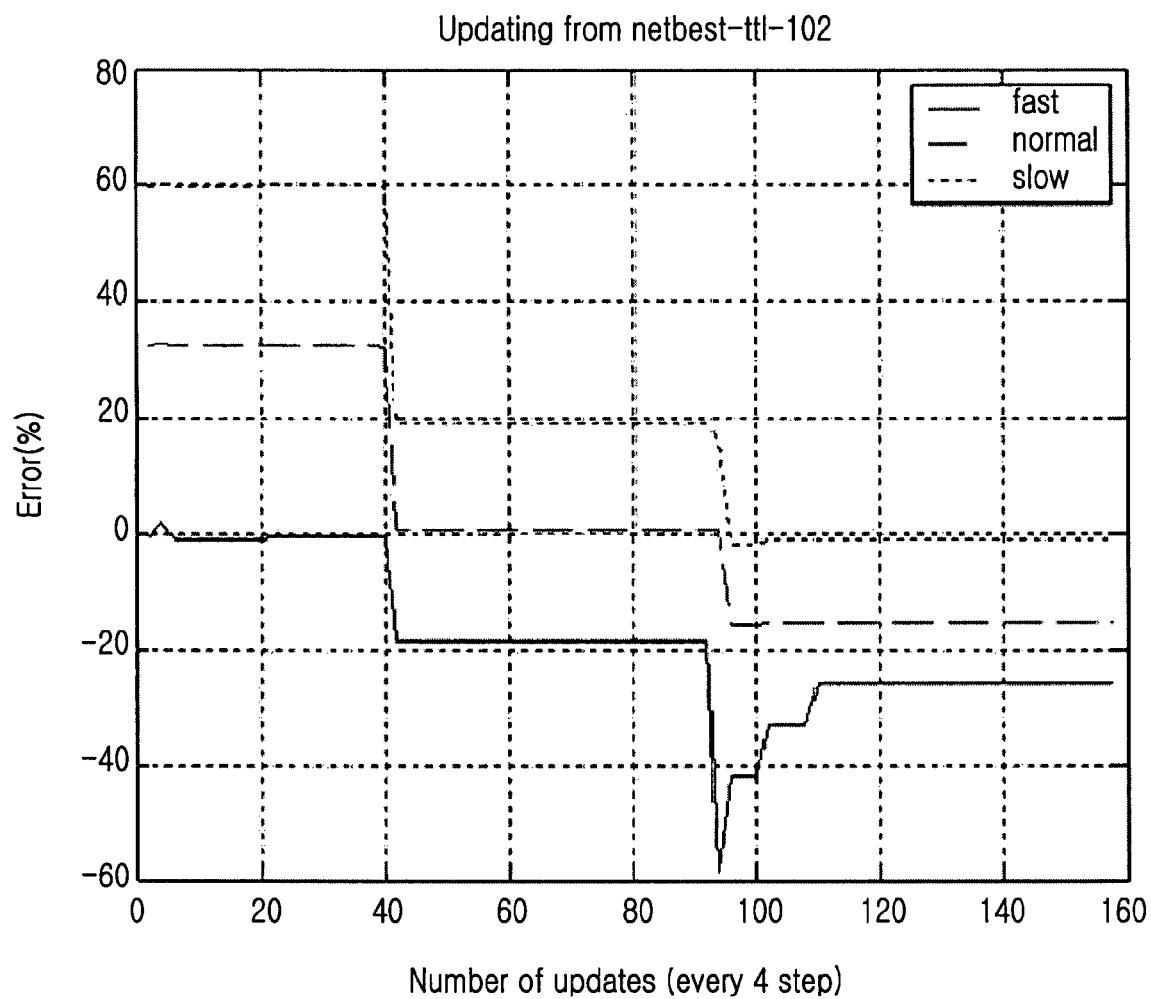

Hereinafter, preferred embodiments of the present invention will be described in detail with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

The present invention provides a plan in which a neural network has been instructed in a walking frequency and an acceleration dispersion using GPS reception signals and acceleration sensor values in a terminal provided with a GPS receiver and an acceleration sensor, and a user's pace can be detected though the neural network having been instructed in the acceleration sensor values at a position where the GPS signals are not received. Further, instruction is provided through the neural network in the present invention, and an instruction data set is subdivided. The instruction data set can have nine walking pattern groups where three classifications divided with a walking velocity are subdivided into three classifications divided with acceleration sensor information.

Figure 4:
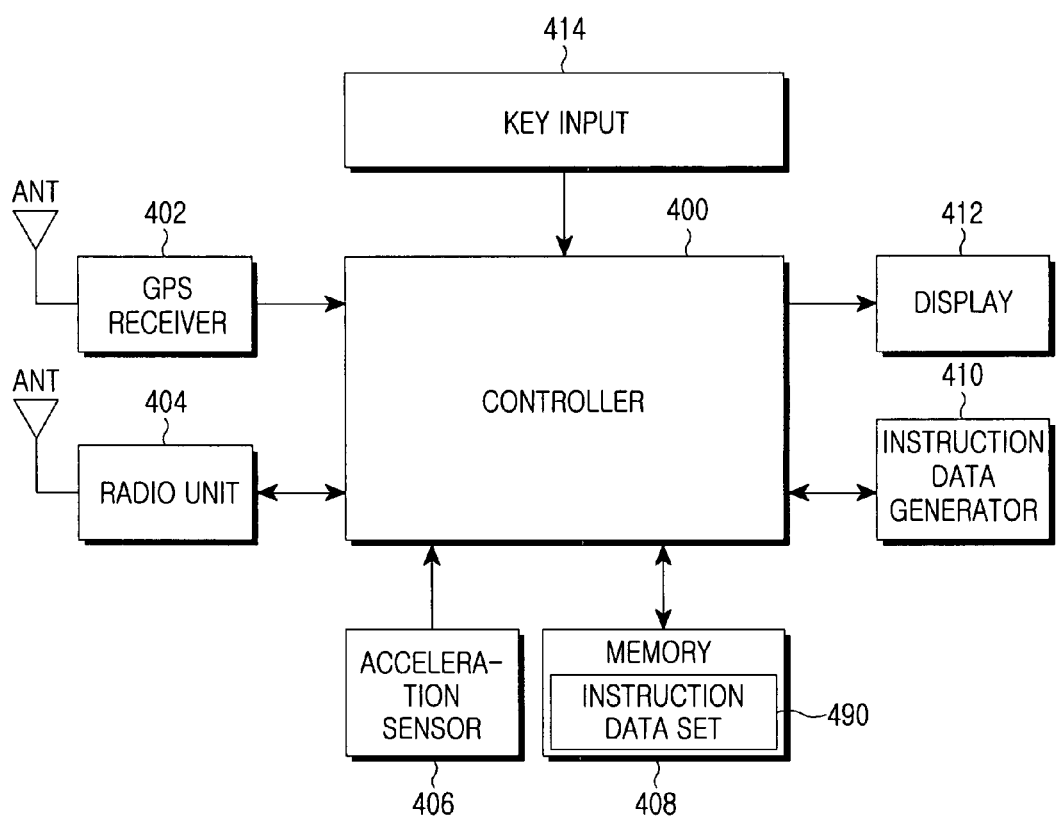
FIG. 4 is a block diagram illustrating a configuration of a mobile communication terminal for detecting an adaptive pace according to the present invention.

The representative value of each of the walking pattern groups is obtained through instruction. Here, the acceleration sensor information can be yielded by measuring a user's movement, i.e., vibration due to walking. FIG. 4 is a block diagram illustrating a configuration of a mobile communication terminal for detecting an adaptive pace according to the present invention. The mobile communication terminal includes a display 412 for displavina information outnut from controller 400, a key input 414 for inputtina keys to controller 400, an acceleration sensor 406 and an instruction data generator 410.

Controller 400 controls the general operation of the mobile communication terminal. Controller 400 detects a pace with an acceleration sensor value at a position where a GPS reception signal is not received so a movement distance value can be output referring to instruction data set 490, in which instruction data, produced in instruction data generator 410, is stored. An operation of controller 400 will be discussed in more detail below with reference to FIG. 8.

GPS receiver 402 receives GPS signals from a GPS satellite through an antenna such that it can immediately grasp the position of the mobile communication terminal. In other words, the mobile communication terminal receives GPS position information transmitted from the GPS satellite through GPS receiver 402.

Radio unit 404 generally performs radio communications with a station.

Acceleration sensor 406 may be built in Micro Electro Mechanical Systems (MEMS), i.e., a personal navigation equipment such as a cellular phone or a PDA as a microminiature accelerometer sensor, and configured such that acceleration sensor 406 can sense acceleration with at least two axes. Such an acceleration sensor 406 can sense linear motion with respect to a lateral direction (X), a progressing direction (Y) and a gravity direction (Z) of a walker, and can output an acceleration signal corresponding to each sensed result. Memory 408 may be composed of a Read Only Memory (ROM) for storing a plurality of programs and data, a Random Access Memory (RAM) and the like. Memory 408, according to the present invention, stores instruction data set 490. Instruction data set 490 is a data set in which walking pattern groups are divided depending on a velocity of a pace and there exists a walking pattern representative value and a walking pattern mean value. This will be discussed in more detail with reference to FIGS. 5 and 6. In the present invention, the walking pattern group will be divided into nine groups. However, such a walking pattern group may have greater or less than nine groups depending on conditions.

Figure 5:
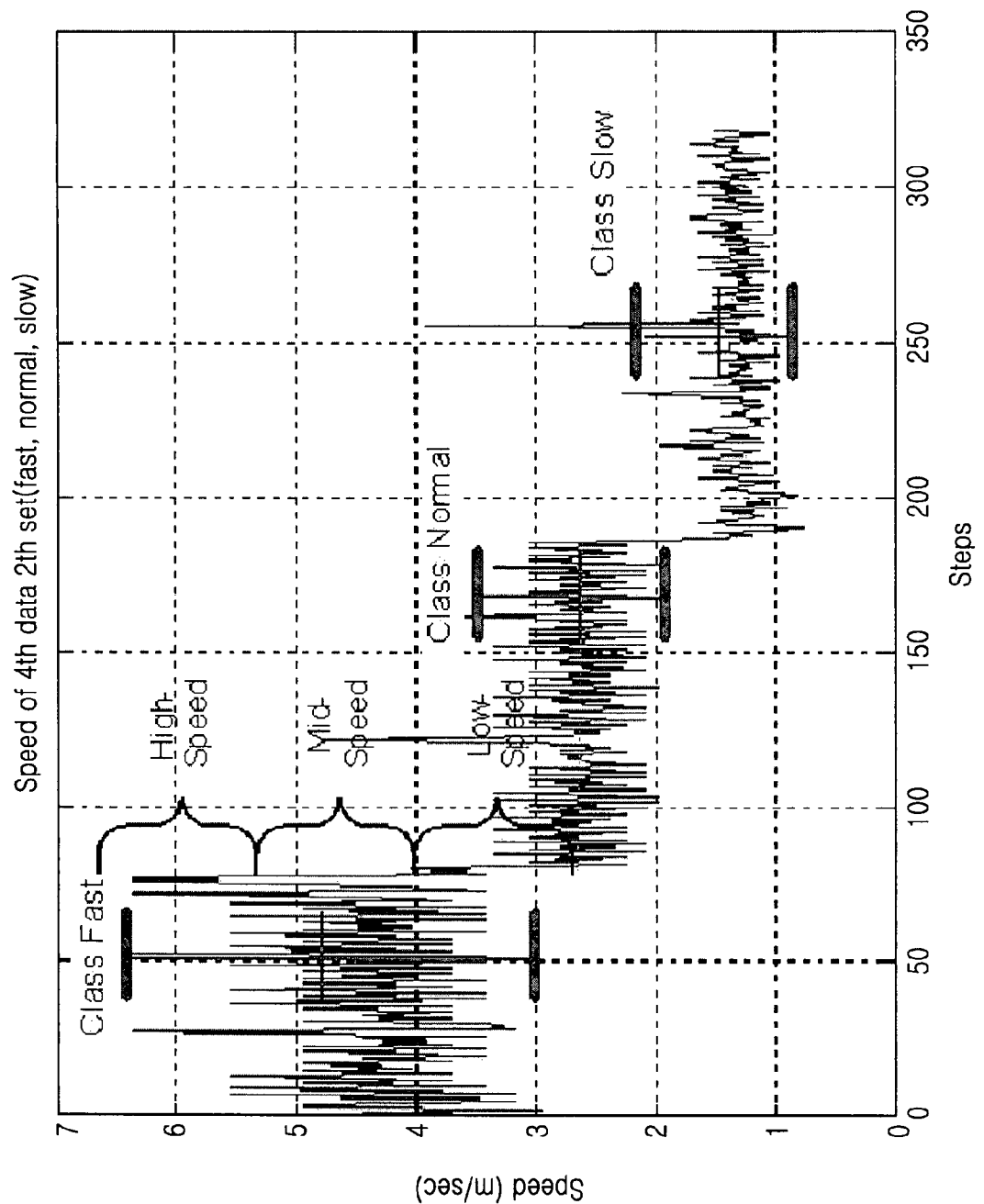
FIG. 5 is a view illustrating a walking pattern group classified depending on a pace and a velocity according to the present invention.

Referring to FIG. 5, a walking pattern group classified depending on a pace and a velocity is illustrated. It can be seen that a data input with a velocity of about 3 m/s to 6.5 m/s is classified into a fast pace group; a data input with a velocity of about 2 m/s to 3 m/s is classified into a normal pace group; and a data input with a velocity of about 1 m/s to 2 m/s is classified into a slow pace group. The acceleration dispersion of an acceleration sensor output in each of the fast, normal and slow pace groups is classified into three groups of high-speed, mid-speed and low-speed steps. A deviation of the acceleration dispersion and the walking frequency is large within a group with similar paces. Thus, in order to minimize the difference of detected paces in accordance with this deviation, it is necessary to divide the group again with each of the fast, normal and slow pace groups. Since a user's usual pace is not uniform depending on a walking velocity and has a deviation larger than expected, deviation of acceleration dispersion and walking frequency result from the walking velocity. Therefore, the walking pattern group performs a classification depending on a velocity in the present invention. That is, each of the fast, normal and slow pace groups is divided into acceleration dispersion values of high-speed, mid-speed and low-speed steps to configure a total of nine groups.

Figure 6:
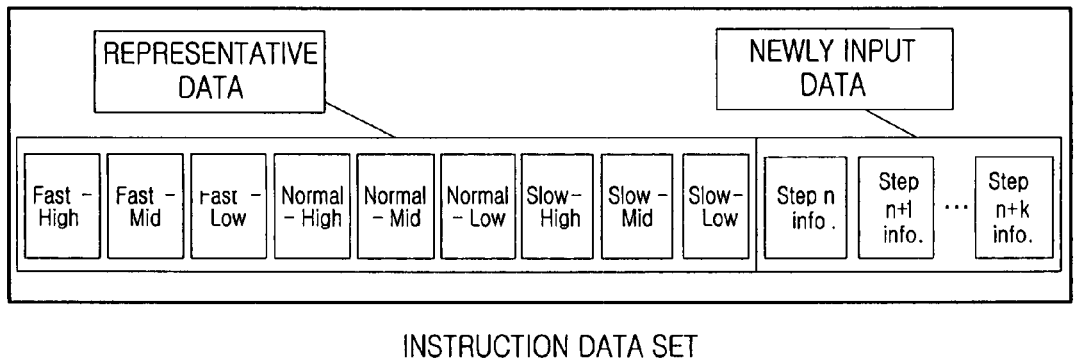
FIG. 6 is a view showing instruction data sets according to the present invention.

FIG. 6 are views showing instruction data sets according to the embodiment of the present invention. View (a) of FIG. 6 shows an internal configuration of instruction data set 490 stored in memory 408, where instruction data set 490 includes representative data of the respective walking pattern groups and stores newly input data. Referring to view (b) of FIG. 6, each of the walking pattern groups has a walking pattern representative value and a walking pattern mean value, in which each of the walking pattern representative value and the walking pattern mean value are composed of a step frequency and an acceleration dispersion value. Meanwhile, instruction data generator 410 generates instruction data using GPS reception signals and acceleration sensor values so as to estimate an adaptive pace under the control of controller 400. An operation of instruction data generator 410 will be discussed in more detail below with reference to FIG. 7.

Figure 7:
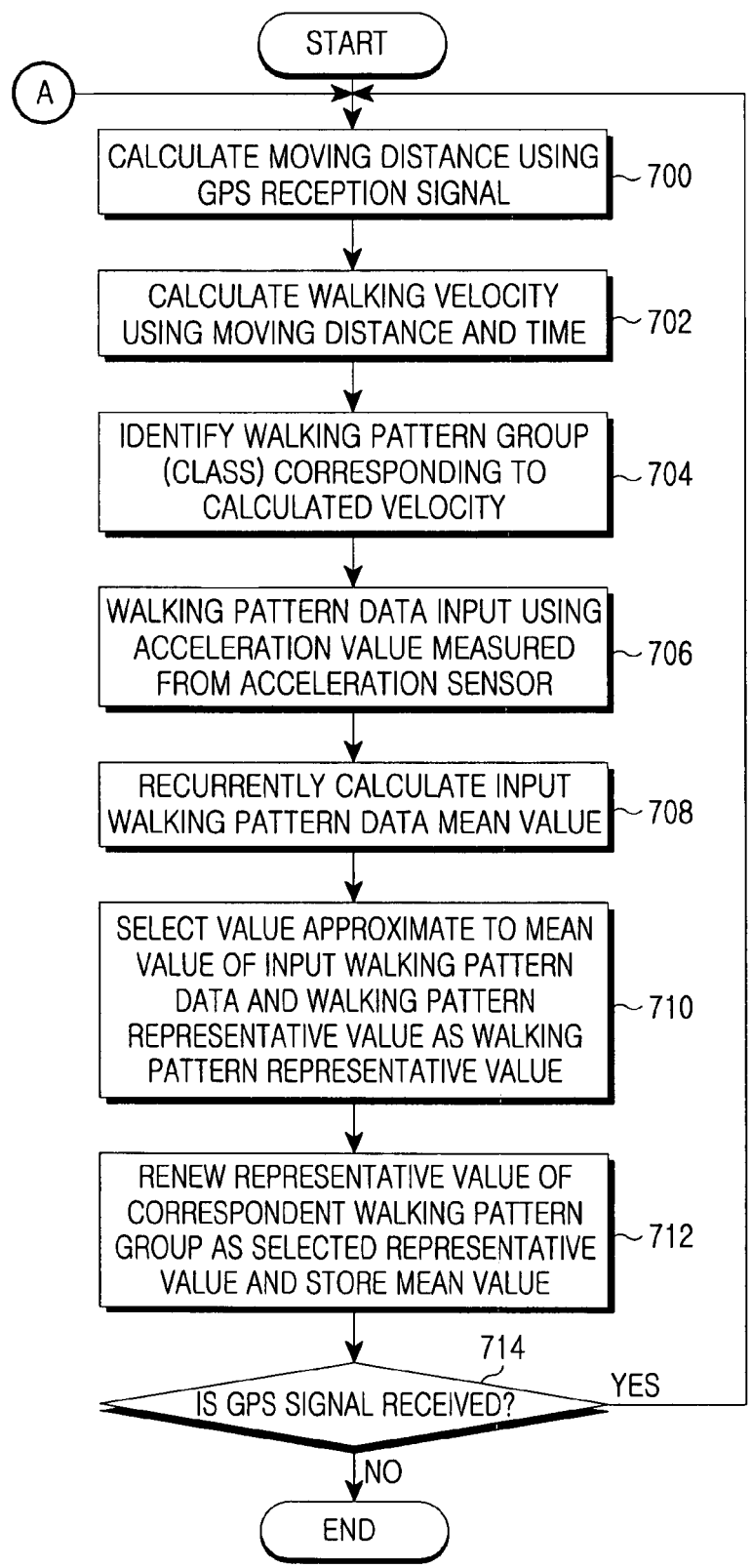
FIG. 7 is a flowchart illustrating an operation of generating an instruction data set for an adaptive pace estimation when receiving GPS signals according to the present invention.

FIG. 7 is a flowchart illustrating an operation of generating an instruction data set for an adaptive pace estimation when receiving GPS signals according to the present invention. The operation in FIG. 7 is an operation of generating instruction data for an adaptive pace estimation using GPS signals and acceleration sensor values in instruction data generator 410.

First, instruction data generator 410 calculates a moving distance using a GPS reception signal at step 700. For example, assuming that a GPS reception period is one second, the GPS signal is received every second, and the moving distance for one second is evaluated using the current position value and the position value after one second elapses.

Thereafter, instruction data generator 410 calculates a walking velocity using the moving distance and times at step 702, and proceeds to step 704 to identify a walking pattern group corresponding to the calculated walking velocity. For example, assuming that it is a walking pattern group classified as shown in FIG. 5 and view (b) of FIG. 6, if the walking velocity calculated at step 702 is 5 m/s, instruction data generator 410 identifies that it belongs to the second walking pattern group. Here, information on a moving distance, time, a walking velocity, which are calculated using a GPS reception signal, refers to walking information in the present invention.

At this time, instruction data generator 410 generates a representative value using a sensor value measured from acceleration sensor 406 at step 706. The representative value is a vector value of a walking frequency and an acceleration dispersion value as a walking pattern representative value. Since a method of calculating the walking frequency and the acceleration dispersion value from the acceleration sensor value is readily understood by those skilled in the art, it will be omitted in the present invention. Further, although not shown in FIG. 7, in a case where the representative value generated at this time is a representative value firstly input to a correspondent walking pattern group, it is immediately stored and the instruction data generator 410 proceeds to step 714.

In a case where there exists the previous representative value stored in the correspondent walking pattern group after the representative value has been generated at step 706, a walking pattern data mean value input to the correspondent walking pattern group is calculated at step 708. The mean value of input values is calculated using Equation (1).

$$m(k) = m(k-1)\frac{k-1}{k} + \frac{x(k)}{k} \qquad \text{Equation (1)}$$

In Equation (1), m(k) denotes a vector mean value in a case where there exist data input to the walking pattern group in a $k^{th}$ order, and x(k) is data input to the walking pattern group in a $k^{th}$ order. At this time, the input data is a vector value of a walking frequency and an acceleration dispersion, which are calculated from an acceleration value measured through acceleration sensor 406. Further, m(k-1) means the previous mean value stored in the memory 408 in a case where there exist data input to the walking pattern group in a $(k-1)^{th}$ order and there are generated $k^{th}$ input data as a vector mean value.

Instruction data generator 410 calculates the mean value in the above mentioned manner, and selects a value approximate to the mean value from the input walking pattern data and walking pattern representative value so as to update the approximate value as a new walking pattern representative value at step 710. More specifically, instruction data generator 410 calculates a first vector value in which a vector difference between the mean value and the walking pattern representative value stored in the memory 408 is calculated and a second vector value in which a vector difference between the mean value and the currently input walking pattern data is calculated, and then compares absolute values of the first and second vector values to select a walking pattern representative value that the absolute value corresponds to the vector value.

Thereafter, instruction data generator 410 proceeds to step 712 to renew the representative value selected at step 710 as a representative value of the correspondent walking pattern group and to store the mean value calculated at this time.

Thereafter, if a GPS signal is received at step 714, instruction data generator 410 proceeds to step 700 to optimize instruction data for pace estimation while continuously updating the representative value of the walking pattern group. Instruction data generator 410 generates the instruction data for pace estimation to store them in the area of the instruction data set 490 in the memory 408.

Figure 8:
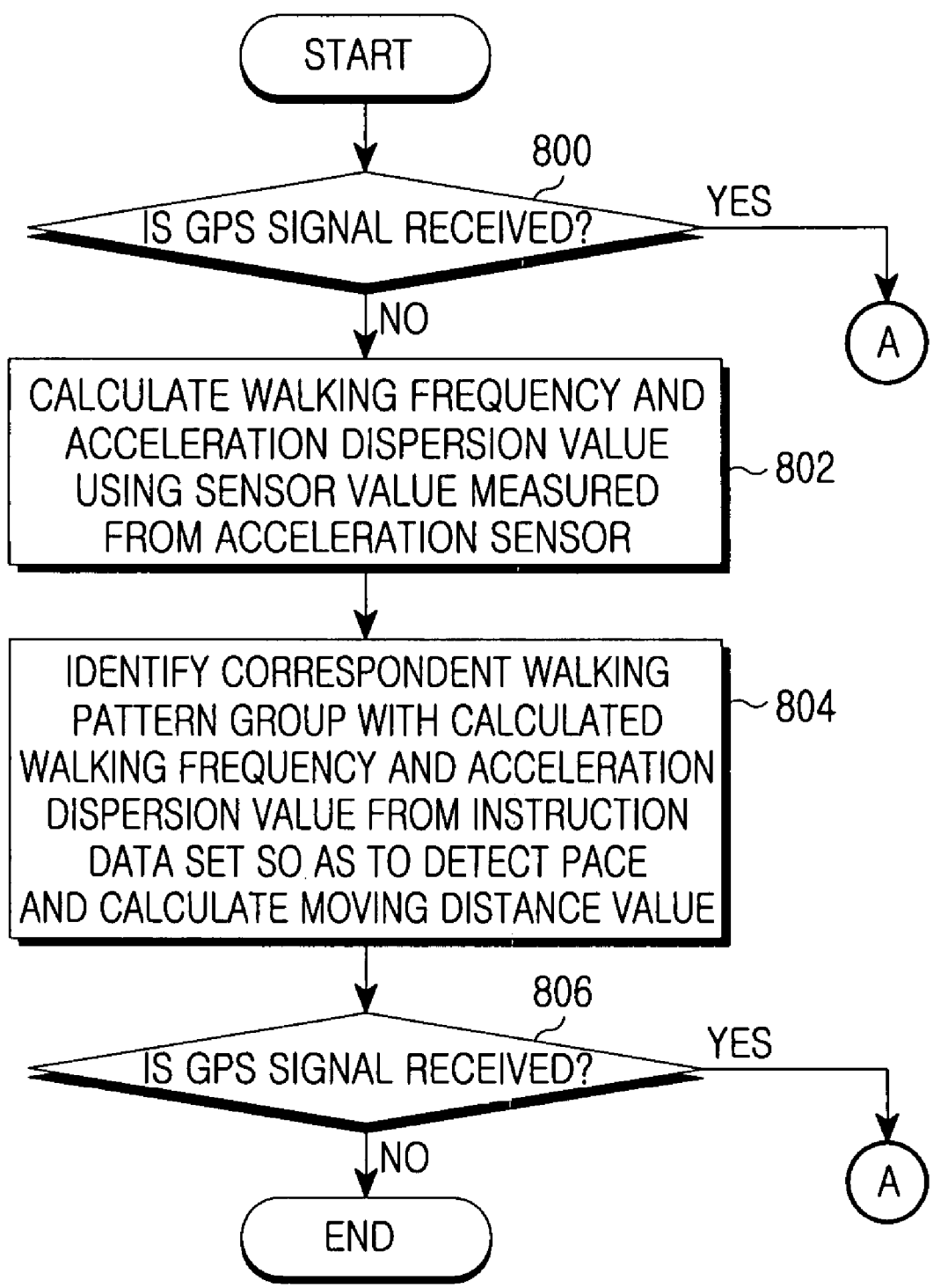
FIG. 8 is a flowchart illustrating an operation of estimating a pace using an acceleration sensor value according to the present invention.

Then, a process of detecting a pace using an acceleration sensor value in a case where a user with the mobile communication terminal shown in FIG. 4 is located at a location where a GPS signal is not received in a state where instruction data for a pace estimation are stored as an optimized status through an operation described in FIG. 7, will be discussed with reference to FIG. 8. FIG. 8 shows an operation of estimating a pace using an acceleration sensor value according to the present invention.

First, controller 400 examines whether a GPS signal is received at step 800. If a GPS signal is received, the controller 400 proceeds to step 700 of FIG. 7 to continuously generate instruction data for a pace estimation. If a GPS signal is not received, controller 400 proceeds to step 802.

Figure 9:
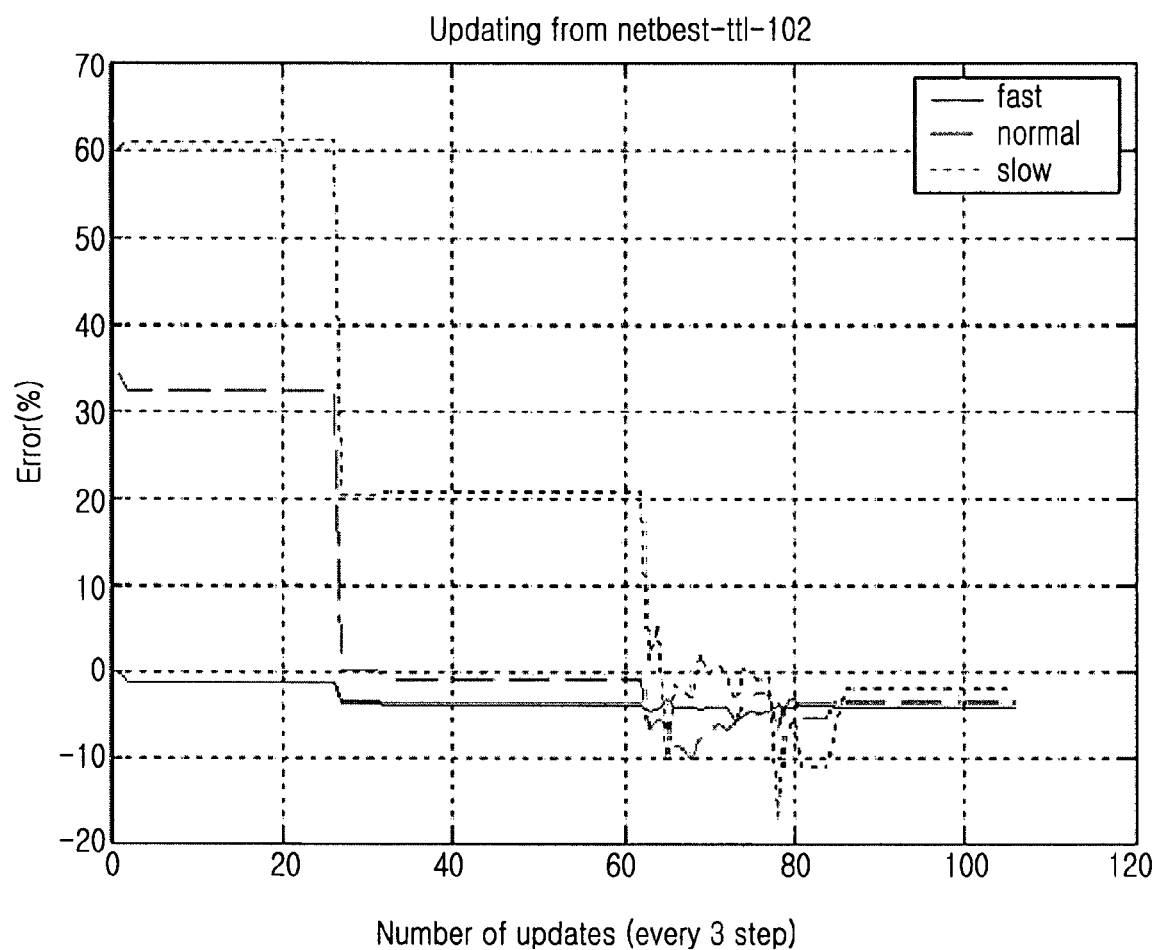
FIG. 9 is an exemplary view illustrating a change in error generated when estimating a pace using instruction data sets according to the present invention.

Controller 400 calculates a walking frequency and an acceleration dispersion value using a sensor value measured from acceleration sensor 406 at step 802. Thereafter, controller 400 identifies a correspondent walking pattern group with the calculated walking frequency and acceleration dispersion value from the instruction data set, so as to detects a pace and yield a moving distance value in step 804. At this time, the controller 400 examines again whether a GPS signal is received in step 806. If the GPS signal is received, the controller proceeds to step 700 of FIG. 7 and the moving distance value can be yielded by a neural network process using an instruction data set with a walking pattern representative value as shown in FIG. 7 updated in accordance with an instruction corresponding to the walking pattern, If a pace is detected using the instruction data generated to estimate an adaptive pace as described above, it can be seen that an error rate does not substantially change and approaches 0% as shown in FIG. 9.

Controller 400 calculates a walking frequency and an acceleration dispersion value using a sensor value measured from acceleration sensor 406 at step 802. Thereafter, controller 400 identifies a correspondent walking pattern group with the calculated walking frequency and acceleration dispersion value from the instruction data set, so as to detects a pace and yield a moving distance value in step 804. At this time, the controller 400 examines again whether a GPS signal is received in step 806. If the GPS signal is received, the controller vroceeds to step 700 of FIG. 7 and the moving distance value can be yielded by a neural network process using an instruction data set with a walking pattern representative value as shown in FIG. 7 updated in accordance with an instruction corresponding to the walking pattern group. If a pace is detected using the instruction data generated to estimate an adaptive pace as described above, it can be seen that an error rate does not substantially change and approaches 0% as shown in FIG. 9.

As described above, the present invention has an advantage in that a neural network adaptively instructed in a walking frequency and an acceleration dispersion for a user using GPS reception signals and acceleration sensor values in a terminal provided with a GPS receiver and an acceleration sensor, and the pace of the user can be detected at a location where the GPS signal is not received through the neural network having been instructed in the acceleration sensor value, so that the velocity distribution of a walker can be precisely obtained to estimate a pace.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. An adaptive pace estimation device, comprising:
a Global Positioning System (GPS) receiver for receiving position information from a GPS satellite;
an acceleration sensor for measuring vibrations due to walking to output an acceleration value used to determine walking pattern data;
a memory for storing an instruction data set with a walking pattern representative value updated in accordance with an instruction corresponding to at least one walking pattern group; and
an instruction data generator for calculating a mean of said input walking pattern data and for updating the walking pattern representative value by choosing a data value from the input walking pattern data and the walking pattern representative value which is approximate said calculated mean.

2. The pace estimation device as claimed in claim 1, wherein the walking pattern group is a group in which at least one group divided with a walking velocity as a reference are subdivided with the acceleration value as a reference.

3. The pace estimation device as claimed in claim 2, wherein the mean is calculated as $$m(k) = m(k-1)\frac{k-1}{k} + \frac{x(k)}{k}$$

wherein m(k) denotes a vector mean of a walking pattern representative value in a case where there exists the walking pattern representative value input to the walking pattern group in a $k^{th}$ order; x(k) denotes a walking pattern representative value input to the walking pattern group in a $k^{th}$ order; and m(k-1) means the previous mean stored in the memory in a ease where there exists a walking pattern representative value input to the walking pattern group in a $(k-1)^{th}$ order and there are generated $k^{th}$ input data as a vector mean.

4. The pace estimation device as claimed in claim 1, wherein the instruction data generator calculates the mean of the walking pattern data from signals output from the GPS receiver and the acceleration sensor; calculates a first vector value in which a vector difference between the mean and the walking pattern representative value stored in the memory is calculated and a second vector value in which a vector difference between the mean and the currently input walking pattern data is calculated; and then compares absolute values of the first and second vector values to update a walking pattern representative value so that the absolute values correspond to the vector values as the walking pattern representative value in the memory.

5. The pace estimation device as claimed in claim 1, wherein the walking pattern representative value includes a walking frequency value and an acceleration dispersion value, which represent a correspondent walking velocity.

6. The pace estimation device as claimed in claim 1, further comprising a controller for inputting an acceleration value measured from the acceleration sensor in walking to a neural network having been instructed using the instruction data set stored in the memory to estimate the pace of a walker and to yield a moving distance value unless a GPS signal is not received.

7. A method for estimating pace in a communication terminal provided with a Global Positioning System (GPS) receiver for receiving position information from a GPS satellite and an acceleration sensor for measuring vibrations due to walking to output an acceleration value, comprising:
storing an instruction data set with a walking pattern representative value updated in accordance with an instruction corresponding to at least one walking pattern group;
calculating a mean of input walking pattern data; and
updating the walking pattern representative value by choosing a data value from the input walking pattern data and the walking pattern representative value which is approximate said calculated mean.

8. The method as claimed in claim 7, wherein the walking pattern group is a group in which at least one group divided with a walking velocity as a reference are subdivided with the acceleration value as a reference.

9. The method as claimed in claim 7, wherein the calculating step calculates the mean of the walking pattern data from signals output from the GPS receiver and the acceleration sensor.

10. The method as claimed in claim 7, wherein the updating step comprises:
calculating a first vector value in which a vector difference between the mean and the walking pattern representative value stored in the memory is calculated and a second vector value in which a vector difference between the mean and the currently input walking pattern data is calculated; and comparing the stored walking pattern representative value with absolute values of the first and second vector values in order to update the walking pattern representative value so that the absolute values correspond to the vector values as a walking pattern representative value in the memory.

11. The method as claimed in claim 7, wherein the walking pattern representative value includes a walking frequency value and an acceleration dispersion value, which represent a correspondent walking velocity.

12. The method as claimed in claim 7, wherein the mean is calculated as $$m(k) = m(k-1)\frac{k-1}{k} + \frac{x(k)}{k}$$

wherein m(k) denotes a vector mean of a walking pattern representative value in a case where there exists the walking pattern representative value input to the walking pattern group in a $k^{th}$ order; x(k) denotes a walking pattern representative value input to the walking pattern group in a $k^{th}$ order; and m(k-1) means the previous mean stored in the memory in a case where there exists a walking pattern representative value input to the walking pattern group in a $(k-1)^{th}$ order and there are generated $k^{th}$ input data as a vector mean.

13. The method as claimed in claim 7, further comprising inputting an acceleration value measured from the acceleration sensor in walking to a neural network having been instructed using the instruction data set stored in the memory to estimate a pace of a walker and to yield a moving distance value unless a GPS signal is not received.

* * * * *